(12) United States Patent
Peterson (10) Patent No.: US 9,446,239 B2
(45) Date of Patent: Sep. 20, 2016

(54) FIELD AUGMENTED CURRENT STEERING USING VOLTAGE SOURCES

(71) Applicant: BOSTON SCIENTIFIC NEUROMODULATION CORPORATION, Valencia, CA (US)

(72) Inventor: David K. L. Peterson, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 122 days.

(21) Appl. No.: 13/794,359

(22) Filed: Mar. 11, 2013

(65) Prior Publication Data

US 2013/0245715 A1 Sep. 19, 2013

Related U.S. Application Data

(60) Provisional application No. 61/611,951, filed on Mar. 16, 2012.

(51) Int. Cl.
*A61N 1/36* (2006.01)
*A61N 1/05* (2006.01)

(52) U.S. Cl.
CPC .......... *A61N 1/36071* (2013.01); *A61N 1/0551* (2013.01); *A61N 1/36182* (2013.01)

(58) Field of Classification Search
CPC ............... A61N 1/36125; A61N 1/36071; A61N 1/36182; A61N 1/0551
USPC ................................... 607/46, 117
See application file for complete search history.

(56) References Cited

U.S. PATENT DOCUMENTS 5,285,781 A * 2/1994 Brodard ............... 607/59
6,516,227 B1 2/2003 Meadows et al.
6,895,280 B2 5/2005 Meadows et al.
(Continued)

FOREIGN PATENT DOCUMENTS

JP 2015509817 A 4/2015
WO WO-2013138252 A1 9/2013

OTHER PUBLICATIONS

PCT International Search Report for PCT/US2013/030276, Applicant: Boston Scientific Neuromodulation Corporation, Form PCT/ISA/210 and 220, May 16, 2013 (6pages).
PCT Written Opinion of the International Search Authority for PCT/US2013/030276, Applicant: Boston Scientific Neuromodulation Corporation, Form PCT/ISA/237, dated May 16, 213 (6pages).
(Continued)

*Primary Examiner* — Alyssa M Alter
(74) *Attorney, Agent, or Firm* — Schwegman Lundberg & Woessner, P.A.

(57) ABSTRACT

A neurostimulation comprises a plurality of electrical terminals configured for being respectively coupled to an array of electrodes, at least three configurable sources respectively coupled to at least three of the electrical terminals, and control circuitry configured for programming each of the at least three configurable sources to be either a current source or a voltage source. A method of providing neurostimulation therapy to a patient using an array of electrodes implanted adjacent neural tissue of the patient, comprises conveying electrical stimulation energy between a first one the electrodes and a second one of the electrodes, thereby creating an electrical field potential within the neural tissue, regulating a first current flowing through the first electrode, and regulating a first voltage at a third different one of the electrodes, thereby modifying a shape of the electrical field potential within the neural tissue.

20 Claims, 7 Drawing Sheets

(56) References Cited

U.S. PATENT DOCUMENTS

| | | |
|---|---|---|
| 7,539,538 B2 | 5/2009 | Parramon et al. |
| 7,650,184 B2 | 1/2010 | Walter |
| 8,019,439 B2 | 9/2011 | Kuzma et al. |
| 2003/0139781 A1 | 7/2003 | Bradley et al. |
| 2005/0267546 A1 | 12/2005 | Parramon et al. |
| 2007/0150036 A1 | 6/2007 | Anderson |
| 2007/0168004 A1 | 7/2007 | Walter |
| 2007/0168007 A1 | 7/2007 | Kuzma et al. |
| 2010/0280577 A1* | 11/2010 | Roy .................. A61N 1/36125 607/62 |
| 2010/0331923 A1 | 12/2010 | Peterson |
| 2011/0264171 A1 | 10/2011 | Torgerson |

OTHER PUBLICATIONS

PCT International Preliminary Report on Patentability (Chapter I of the Patent Cooperation Treaty) for PCT/US2013/030276, Applicant: Boston Scientific Neuromodulation Corporation, Form PCT/IB/326 and 373, dated Sep. 25, 2014 (8pages).

"Australian Application Serial No. 2013232394, First Examiner Report mailed Nov. 26, 2014", 4 pgs.

"Japanese Application Serial No. [Pending], Amendment filed Dec. 9, 2014", English version of amended claims, 2.

"Japanese Application Serial No. 2015-500497, Office Action mailed Oct. 20, 2015", With Partial English Translation, 5 pgs.

\* cited by examiner

FIELD AUGMENTED CURRENT STEERING USING VOLTAGE SOURCES

RELATED APPLICATION DATA

The present application claims the benefit under 35 U.S.C. §119 to U.S. provisional patent application Ser. No. 61/611,951, filed Mar. 16, 2012. The foregoing application is hereby incorporated by reference into the present application in its entirety.

FIELD OF THE INVENTION

The present invention relates to tissue stimulation systems.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes an electrode lead implanted at the desired stimulation site and an implantable pulse generator (IPG) implanted remotely from the stimulation site, but coupled either directly to the electrode lead or indirectly to the electrode lead via a lead extension. Thus, electrical pulses can be delivered from the neurostimulator to the stimulation electrode(s) to stimulate or activate a volume of tissue in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, rate, and burst rate of the stimulation pulses.

The neurostimulation system may further comprise a handheld remote control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

Electrical stimulation energy may be delivered from the neurostimulator to the electrodes using one or more current-controlled sources for providing stimulation pulses of a specified and known current (i.e., current regulated output pulses), or one or more voltage-controlled sources for providing stimulation pulses of a specified and known voltage (i.e., voltage regulated output pulses). The circuitry of the neurostimulator may also include voltage converters, power regulators, output coupling capacitors, and other elements as needed to produce constant voltage or constant current stimulus pulses.

Single source current regulated and voltage regulated neurostimulators are highly limited in their ability to shape the current distribution and electric field around the electrode array used to activate excitable tissue. In essence, the electric field is determined by the electrode array geometry and the impedance profile of the surrounding tissue.

Multiple independent current source neurostimulators were developed to address this limitation. These neurostimulator types can be used to more precisely control the current distribution in tissue, and thus more selectively activate excitable tissue. This augments the capability inherent in the electrode array geometry and limits the influence of the surrounding impedance profile. In one technique particularly useful for SCS, three electrodes are rostrocaudally arranged along the spinal cord of the patient, with the center electrode configured as a cathode, and the top and bottom flanking electrodes configured as anodes, thereby focusing the stimulation energy at the spinal cord tissue adjacent the center electrode. The shape of the electric field produced by multiple independent current source neurostimulators, however, is still limited to what can be achieved by superposition of current sources in a conductive medium. In addition, current sources are less capable of controlling the electric field potential, which is determined by tissue impedance. Multiple independent voltage source neurostimulators, in principle, can be used to more precisely control the electric field; however, the currents delivered by the voltage sources change with impedance.

Conventional battery-operated neurostimulators typically apply stimulation pulses to the tissue that are referenced to an internal circuit voltage in the neurostimulator, with a relatively low impedance connection being located between one or more stimulation electrodes and internal circuitry. This relatively low impedance effectively clamps the voltage on these stimulation electrodes to the internal circuit voltage, as described in U.S. patent application Ser. No. 12/821,043, entitled "Symmetrical Output Neurostimulation Device," which is expressly incorporate herein by reference."

Because the voltage at the unregulated side of the electrode will be clamped to the voltage of the internal circuitry, and because the stimulation output circuitry may be unbalanced in that some components in the circuitry (coupling capacitors, protection circuits, etc.) may be present on the cathode side of the circuit but not the anode side of the circuit, or vice versa, the output stimulation circuitry between the cathode and the anode will be asymmetrical, such that the cathode and the anode will be asymmetrically referenced to the internal circuit. For example, a shift in voltage in the output stimulation circuit results in asymmetrical voltage shifts between the anodes and cathodes, as described in U.S. patent application Ser. No. 12/821,043. The asymmetry between anodes and cathodes in the output stimulation circuitry may be associated with undesired side effects during stimulation that lead to reduced patient comfort. In particular, parasitic coupling of the common mode signal to the implantable device can give rise to an additional stimulation signal that is superimposed on the differential stimulation signal.

In addition to the problem of asymmetry in the output stimulation circuit, referencing the voltage at the cathodes and anodes to an internal circuit may require excessive voltage levels at the cathodes and anodes in order to maintain the desired voltage potential therebetween. For example, if the desired voltage potential between a cathode and an anode is 5V, and if the internal voltage is 20V, the voltage at the anode would have to be 25V and the voltage at the cathode would have to be 20V. The increased voltage at the electrodes will increase the voltage relative to the tissue, which may cause problems such as unwanted stimulation and even electro-chemical reactions resulting in corrosion of the electrodes.

There, thus, remains a need for an improved method and system for conveying stimulation to tissue in a controlled manner.

SUMMARY OF THE INVENTION

In accordance with a first aspect of the present inventions, a neurostimulation system comprises a plurality of electrical terminals configured for being respectively coupled to an array of electrodes, at least three configurable sources respectively coupled to at least three of the electrical terminals, and control circuitry configured for programming each of the at least three configurable sources to be either as a current source or a voltage source. The control circuitry may further be configured selecting stimulation magnitude values for the at least three configurable sources. In an optional embodiment, the control circuitry may be configured for programming one of the at least three configurable sources as a positive current source, one of the at least three configurable sources as a negative current source, and one of the at least three configurable sources as a voltage source. The neurostimulation system may comprise monitoring circuitry configured for measuring compliance voltages on electrical terminals to which the positive and negative current sources are coupled, in which case, the control circuitry may be configured for assigning a voltage value to the voltage source that is between the compliance voltages on the electrical terminals. The neurostimulation system may further comprise a housing containing the plurality of electrical terminals and at least three configurable sources.

In accordance with a second aspect of the present inventions, a method of providing neurostimulation therapy to a patient using an array of electrodes implanted adjacent neural tissue (e.g., spinal cord tissue) of the patient is provided. The method comprises conveying electrical stimulation energy between a first one the electrodes and a second one of the electrodes, thereby creating an electrical field potential within the neural tissue, and regulating a first current flowing through the first electrode. The method further comprises regulating a first voltage at a third different one of the electrodes, thereby modifying a shape of the electrical field potential within the neural tissue.

An optional method further comprises regulating a second current through the second electrode, in which case, the first electrode may be an anode and the second electrode may be a cathode. The optional method may further comprise regulating a third current flowing through a fourth one of the electrodes, in which case, the fourth electrode may be an anode, and the cathode may be physically located between the anodes. The optional method may further comprise regulating a second voltage at a fourth one of the electrodes, in which case, the first and second electrodes may be physically located between the third and fourth electrodes. The first and second voltages may be the same. The first voltage may be between compliance voltages on the respective first and second electrodes.

Another optional method further comprises programming a programmable current source coupled to the first electrode to set the first current to a first value, and programming a programmable voltage course coupled to the second electrode to set the first voltage to a first value. A first configurable source may be coupled to the first electrode, a second configurable source may be coupled to the third electrode, and each of the first and second configurable sources can either be configured as a current source or a voltage source, in which case, the method may further comprise configuring the first source as a current source, and configuring the second source as a voltage source.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
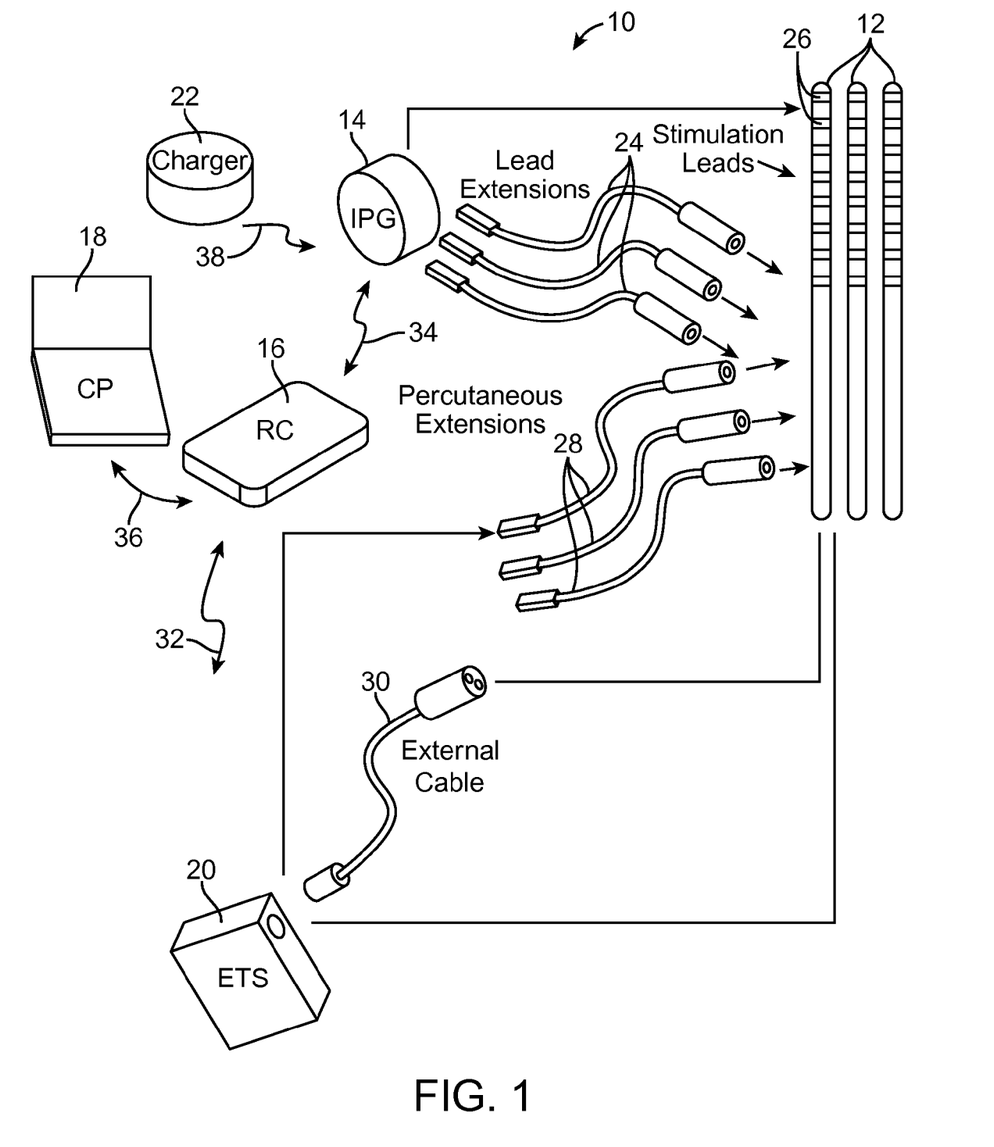
FIG. 1 is a plan view of a Spinal Cord Stimulation (SCS) system constructed in accordance with one embodiment of the present inventions.

Turning first to FIG. 1, an exemplary spinal cord stimulation (SCS) system 10 generally includes one or more (in this case, three) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more lead extensions 24 to the stimulation leads 12, which carry a plurality of electrodes 26 arranged in an array. The stimulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
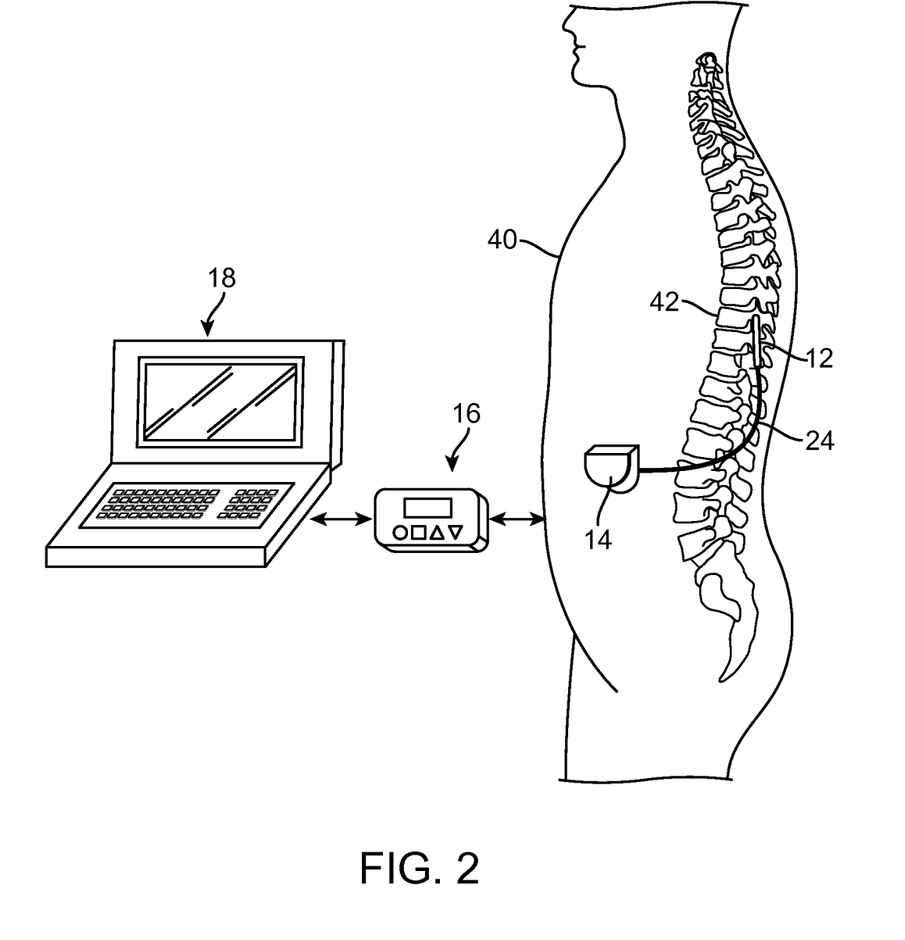
FIG. 2 is a plan view of the SCS system of FIG. 1 in use within a patient.

As shown in FIG. 2, the stimulation leads 12 are implanted within the spinal column 42 of a patient 40. The preferred placement of the electrode leads 12 is adjacent, i.e., resting near, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
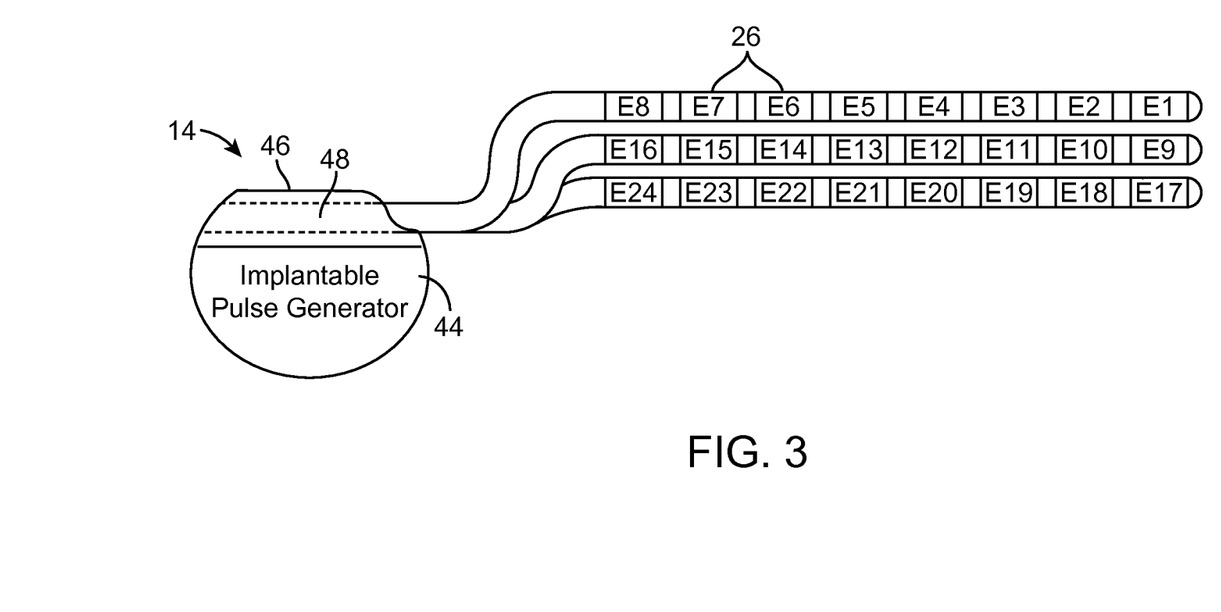
FIG. 3 is a plan view of an implantable pulse generator (IPG) and three percutaneous stimulation leads used in the SCS system of FIG. 1.

Referring now to FIG. 3, the external features of the stimulation leads 12 and the IPG 14 will be briefly described. Each of the stimulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 4:
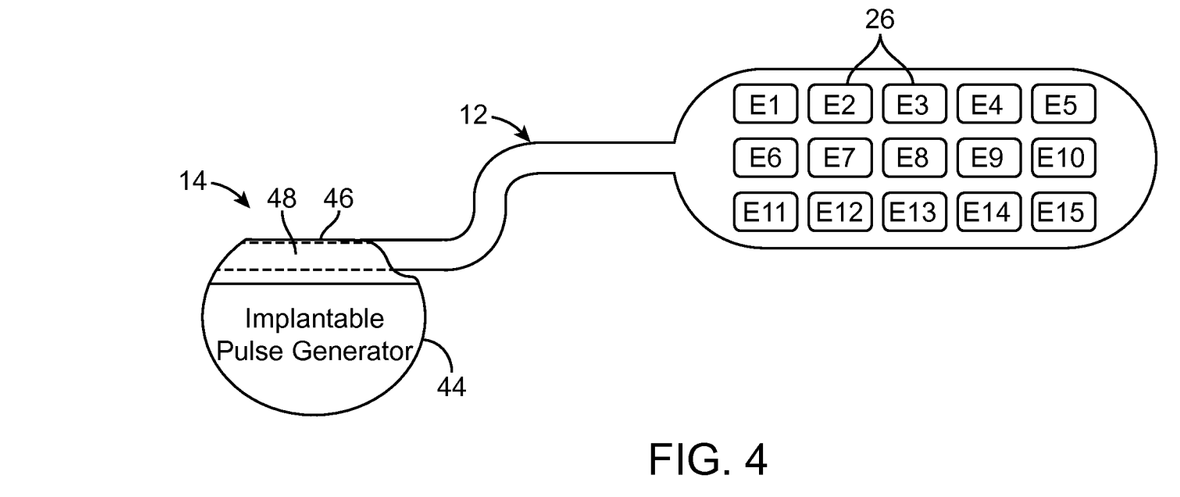
FIG. 4 is a plan view of an implantable pulse generator (IPG) and a surgical paddle lead used in the SCS system of FIG. 2.

Alternatively, as illustrated in FIG. 4, the stimulation lead 12 takes the form of a surgical paddle lead on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 3 and 4, the IPG 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IPG 14 further comprises a connector 46 to which the proximal ends of the stimulation leads 12 mate in a manner that electrically couples the electrodes 26 to the internal electronics (described in further detail below) within the outer case 44. To this end, the connector 46 includes one or more ports (three ports 48 or three percutaneous leads or one port for the surgical paddle lead) for receiving the proximal end(s) of the stimulation lead(s) 12. In the case where the lead extensions 24 are used, the port(s) 48 may instead receive the proximal ends of such lead extensions 24.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 44. Simulation energy may be transmitted to the tissue in a monopolar or multipolar (e.g., bipolar, tripolar, etc.) fashion. Monopolar stimulation occurs when a selected one of the lead electrodes 26 is activated along with the case 44 of the IPG 14, so that stimulation energy is transmitted between the selected electrode 26 and the case 44. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 5:
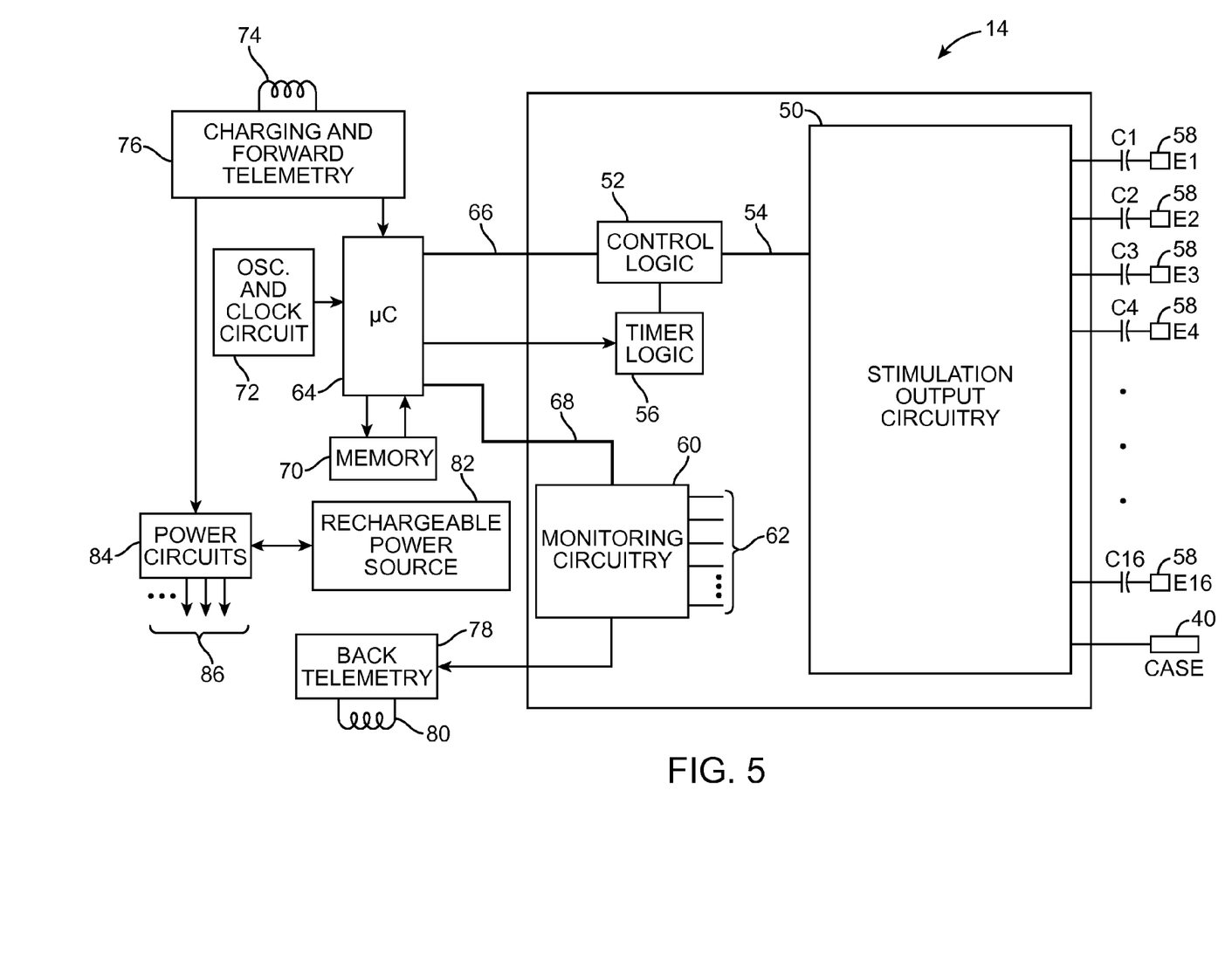
FIG. 5 is a block diagram of the internal components of the IPG of FIG. 5.

Turning next to FIG. 5, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 µs. The stimulation energy generated by the stimulation output circuitry 50 is output via capacitors C1-Cn to electrical terminals 58 corresponding to the electrodes 26.

Figure 6:
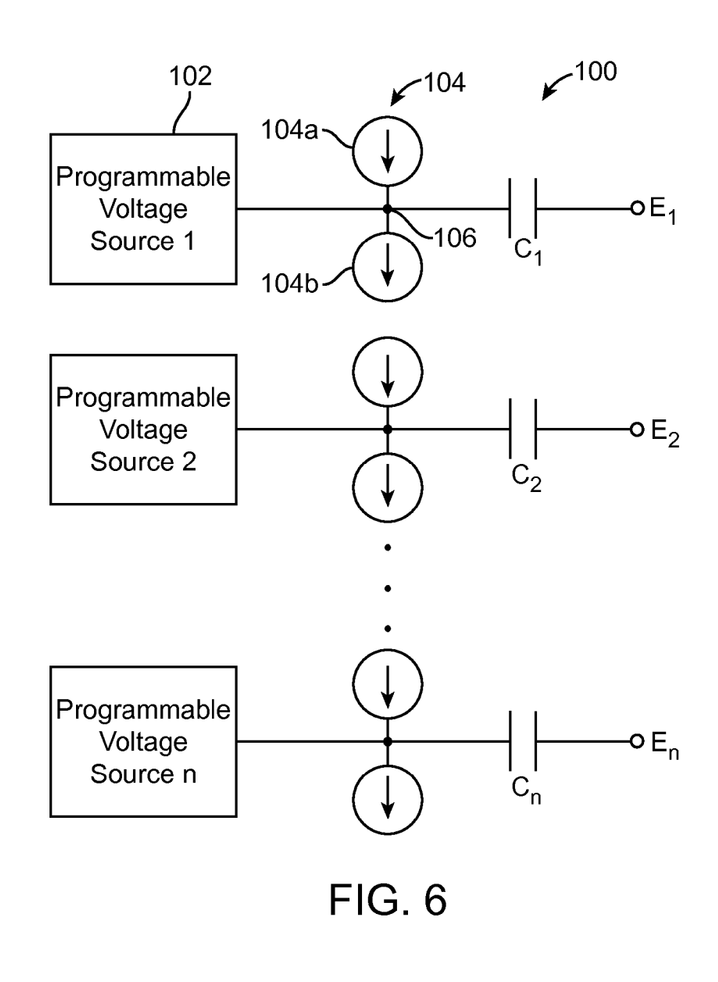
FIG. 6 is a block diagram of programmable hybrid voltage/current sources contained in the stimulation output circuitry of FIG. 5.

As illustrated in FIG. 6, the stimulation output circuitry 50 comprises a plurality of configurable hybrid current/voltage sources 100 for providing stimulation pulses of either a specified and known amperage to or from the electrodes 26 or a specified and known voltage at the electrodes 26. In this manner, each of the electrodes 26 can be operated in either a current source mode or a voltage source mode. In the illustrated embodiment, each of the hybrid sources 100 is dedicated to an electrical terminal 58, and thus, the particular electrode 26 coupled to the electrical terminal 58. Thus, the number of hybrid sources 100 will be equal to the number of electrical terminals 58, and thus the number of electrodes 26.

Alternatively, the number of hybrid sources 100 may be less than the number of electrical terminals 58, and thus less than the number of electrodes 26, in which case, a low impedance switch matrix (not shown) can be coupled between the hybrid sources 100 and the electrical terminals 58, so that any of the hybrid sources 100 may be coupled to the electrical terminals 58, and thus electrodes 26, to be activated. In any event, the number of hybrid sources 100 equals at least three, and preferably at least five, in order to form an electrode configuration comprising a current regulated rostro-caudal anode guarded tripole and two voltage regulated medio-lateral flanking electrodes, as will be described in further detail below.

Each of the hybrid sources 100 comprises a programmable voltage source 102 and a current source pair 104. The voltage source 102 can be programmed to have a positive voltage or a negative voltage. One current source 104a of each pair 104 functions as a positive (+) current source, while the other current source 104b of each pair 104 functions as a negative (−) current source. The outputs of the programmable voltage source 102, and the outputs of the positive current source 104a and the negative current source 104b of each pair 104 are connected to a common node 106. The common node 106 is coupled to the respective one of the electrodes E1-En via the electrical terminals 78. Hence, it is seen that each of the n programmable electrical terminals 78 can be programmed to have a positive voltage, a negative voltage, a positive (sourcing current), a negative (sinking current), or off (no current) polarity. A compliance voltage $V_H$ is supplied to each of the hybrid sources 100. The magnitude of the compliance voltage VH will depend on whether the respective hybrid source 100 is programmed as a voltage source, a positive current source, or a negative current source.

Referring back to FIG. 5, the IPG 14 further comprises monitoring circuitry 60 for monitoring the status of various nodes or other points 62 throughout the IPG 14, e.g., power supply voltages, temperature, battery voltage, and the like. The monitoring circuitry 60 is also configured for measuring electrical parameter data (e.g., electrode impedance and/or electrode field potential). The IPG 14 further comprises processing circuitry in the form of a microcontroller (pC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and stimulation parameters. In controlling the operation of the IPG 14, the microcontroller 64 is able to individually generate stimulus pulses at the electrodes 26 using the stimulation output circuitry 50, in combination with the control logic 52 and timer logic 56, thereby allowing each electrode 26 to be paired or grouped with other electrodes 26, including the monopolar case electrode, to control the polarity, amplitude, rate, pulse width and channel through which the current stimulus pulses are provided.

More specific to the present invention, the microcontroller 64 is capable of programming each of the hybrid sources 100 as either a voltage source or a current source and to further assign the desired stimulation value for the programmed source. In one technique described in further detail below, the microcontroller 64 can program one of the hybrid sources 100 as a positive current source 104a, one of the hybrid sources as a negative current source 104b, and one of the hybrid sources 100 as a voltage source 102. In this case, the monitoring circuitry 60 can measure the compliance voltages on the electrical terminals 78 to which the positive and negative current sources 102 are respectively coupled, and microcontroller 64 is configured for assigning a voltage value to the voltage source 102 that is between the compliance voltages on the electrical terminals 78. In essence, the microcontroller 64 ensures that the voltage output by the voltage source 102 falls within the compliance voltage window of the respective current sources 104, which would otherwise operate as current sources 104 if the output voltage of the voltage source 102 falls outside of the compliance voltage window.

The IPG 14 further comprises an alternating current (AC) receiving coil 74 for receiving programming data (e.g., the operating program and/or stimulation parameters) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, the external charger 22 (shown in FIG. 1), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation energy and background energy in accordance with the control signals.

Having described the structure and function of the SCS system 100, one technique for operating the system 100 to provide therapy to the patient, and in particular, to configure the hybrid sources 100 in a novel manner will now be described. Although the technique described below does not require the use of a hybrid multiple independent current and voltage controlled stimulator output topology, the use of the hybrid sources 100 can be used in a variety of neurostimulator applications to gain better control of the current distribution and electric field than can be provided by dedicated independent current sources and independent voltage sources alone.

In general, electrical stimulation energy is conveyed between at least two electrodes, thereby creating an electric field within the neural tissue is a conventional manner. The hybrid sources 100 coupled to these electrodes are configured as current sources, such that the electrical current flowing through these electrodes is current regulated. In this manner, the current distribution in the tissue targeted for stimulation can be more precisely controlled, thereby more selectively activated the tissue. A first voltage can be regulated at another one of the electrodes, thereby modifying a shape of the electrical field potential within the neural tissue.

For example, as briefly discussed above, and as illustrated in FIG. 7, the hybrid sources 100 can be configured to form an electrode configuration comprising a current regulated rostro-caudal anode guarded tripole and two voltage regulated medio-lateral flanking electrodes; that is, the hybrid source 100 coupled to the center electrode $E_C$ is configured as a negative current source, such that this electrode is activated as a cathode, the hybrid sources 100 respectively coupled to the vertically flanking upper and lower electrodes $E_U$, $E_L$ are configured as positive current sources, such that these electrodes are activated as anodes, and the hybrid sources 100 respectively coupled to the horizontally flanking electrodes $E_L$, $E_R$ are configured as voltage sources. In the exemplary embodiment, the center electrode $E_C$ sinks a current regulated value of −4 mA, each of the vertically flanking electrodes $E_U$, $E_L$ source a current regulated value of +2 mA, and each of the horizontally flanking electrodes $E_L$, $E_R$ has a voltage regulated value of +2V. The current-regulated rostro-caudal tripole can be used to stimulate dorsal column (DC) nerve fibers within the spinal cord of the patient, while the voltage-regulated pair of electrodes can be used to suppress stimulation of the dorsal root (DR) nerve fibers.

Notably, as discussed above, it is important that each of the voltage values at horizontally flanking electrodes $E_L$, $E_R$, when reference to the ground of the IPG 14, fall within the compliance voltage window of the current regulated tripole; that is, the voltage values at the horizontally flanking electrodes $E_L$, $E_R$ are regulated, such that they are between the minimum compliance voltage at the pertinent electrode of the current-regulated tripole and the maximum compliance voltage at the pertinent electrode of the current-regulated tripole. In this manner, the programmed current sources that regulate the current at the tripole will continue to operate as current sources. In the exemplary case illustrated in FIG. 7, the vertically flanking electrodes $E_U$, $E_L$ that source +2 mA are at a voltage potential that is greater than +2V, and the center electrode $E_C$ that sinks −4 mA is at a voltage potential that is less than +2V.

Figure 7:
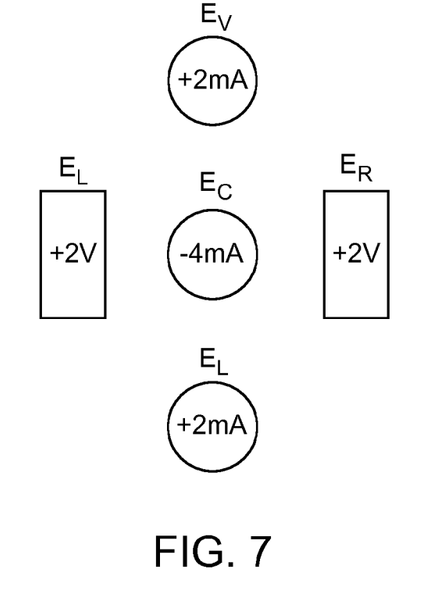
FIG. 7 is a plan view of current regulated and voltage regulated electrodes in accordance one preferred technique of delivering stimulation energy to the patient using the SCS system of FIG. 1.

Furthermore, the current values of the tripole (i.e., electrodes $E_C$, $E_L$, $E_R$) preferably sum to zero (e.g., +2 mA+2 mA−4 mA=0 as shown in FIG. 7), and the respective voltage values at the horizontally flanking electrodes $E_L$, $E_R$ are the same (2V=2V as shown in FIG. 7). In this scenario, no net current flows through the electrodes associated with the voltages sources (in this case, the horizontally flanking electrodes $E_L$, $E_R$), although the voltage potentials at these electrodes influence the current distribution in the tissue created by the current-regulated tripole. In the cases where the current values of the current-regulated electrodes do not sum to zero or the voltage potentials at the voltage regulated electrodes are not equal, the electrical current will flow through the voltage regulated electrodes in accordance with the electric field and the surrounding impedance profile.

Figure 8:
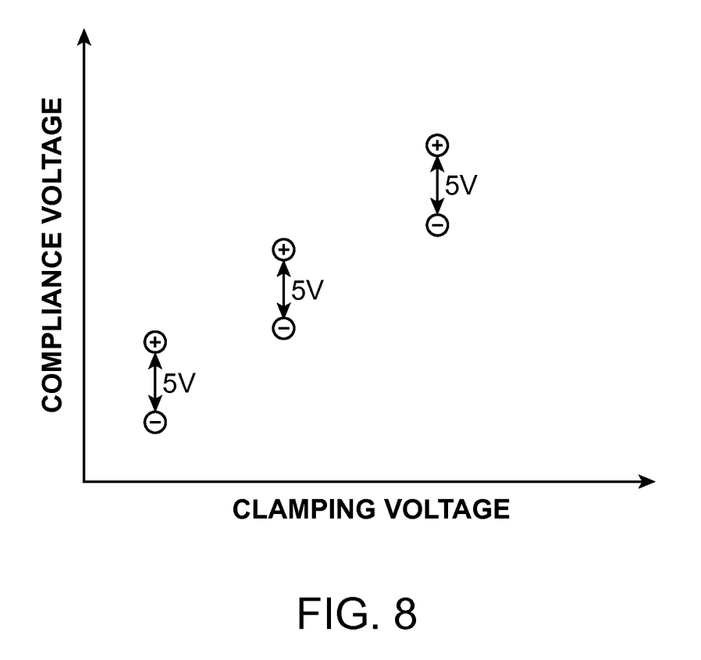
FIG. 8 is a diagram illustrating one preferred technique for voltage clamping current-regulated electrodes using voltage-regulated electrodes.

In addition to providing the capability of reshaping the electric field generated by the current-regulated electrodes, the voltage-regulated electrodes provides the ability to adjust the voltage to which the current-regulated electrodes are clamped, as opposed to the case where the voltage of the current-regulated electrodes would be clamped to the output circuitry of the IPG 14. For example, as illustrated in FIG. 8, the minimum and maximum compliance voltages at two current regulated electrodes can be adjusted up or down by adjusting the clamping voltage of the voltage-regulated electrodes. In the embodiment illustrated in FIG. 8, a 5V difference between the current-regulated electrodes is required to generate the required regulated current flow. The voltage at the voltage-regulated electrodes may be adjusted upward to increase the respective voltages at the current-regulated electrodes, or adjusted downward to decrease the respective voltages at the current-regulated electrodes.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system, comprising:
at least one lead to provide an array of electrodes;
a plurality of electrical terminals configured to be electrically connected to the array of electrodes via the at least one lead;
at least three configurable sources respectively coupled to at least three of the electrical terminals, each of the configurable sources including a current source and a voltage source and each of the configurable sources being capable of being programmed to operate as the current source and being capable of being programmed to operate as the voltage source; and
control circuitry configured for programming each of the at least three configurable sources to be either the current source or the voltage source, wherein the control circuitry is configured to:
program at least one of the configurable sources to operate as the current source and to connect the current source to at least one electrode in the array of electrodes to generate a current distribution in neural tissue; and
program at least one other of the configurable sources to operate as the voltage source and to connect the voltage source to at least one other electrode in the array of electrodes to shape the current distribution.

2. The neurostimulation system of claim 1, wherein the control circuitry is further configured for selecting stimulation magnitude values for the at least three configurable sources.

3. The neurostimulation system of claim 1, wherein the at least three configurable sources comprises four configurable sources.

4. The neurostimulation system of claim 1, wherein the at least three configurable sources comprises five configurable sources, wherein the system is configured to program three of the five configurable sources as current sources and to connect them to the plurality of electrodes to provide a current-regulated rostro-caudal anode guarded tripole, and the system is configured to program two of the five configurable sources a voltage source and to connect them to the plurality of electrodes to provide two voltage-regulated media-lateral flanking electrodes.

5. The neurostimulation system of claim 1, wherein the control circuitry is configured for programming one of the at least three configurable sources as a positive current source, one of the at least three configurable sources as a negative current source, and one of the at least three configurable sources as a voltage source.

6. The system of claim 5, wherein the current-regulated rostro-caudal anode guarded tripole is configured to generate the current distribution to stimulate dorsal column (DC) nerve fibers, and the media-lateral flanking electrodes are configured to modify the shape of the current distribution to suppress stimulation of dorsal root (DR) nerve fibers.

7. The neurostimulation system of claim 5, further comprising monitoring circuitry configured for measuring compliance voltages on electrical terminals to which the positive and negative current sources are coupled, and the control circuitry is configured for assigning a voltage value to the voltage source that is between the compliance voltages on the electrical terminals.

8. The neurostimulation system of claim 1, further comprising an array of electrodes, wherein the plurality of electrical terminals are configured to be respectively coupled to the array of electrodes.

9. The neurostimulation system of claim 1, further comprising a housing containing the plurality of electrical terminals and at least three configurable sources.

10. The system of claim 1, wherein the control circuitry is configured to program at least two of the configurable sources to operate as current sources and connect between at least two of the plurality of electrodes to generate the current distribution, and to program at least two of the configurable sources to operate as voltage sources and connect to at least two of the plurality of electrodes to modify the shape of the current distribution between the at least two of the electrodes.

11. The system of claim 10, wherein the control circuitry is configured program at least two configurable sources to operate as voltage sources to provide equal potentials.

12. A method of providing neurostimulation therapy to a patient using at least three configurable sources respectively coupled to at least three electrical terminals and using at least one lead to provide an array of electrodes adjacent neural tissue of the patient, wherein each of the configurable sources includes a current source and a voltage source and each of the configurable sources being capable of being programmed to operate as the current source and being capable of being programmed to operate as the voltage source, and wherein the array of electrodes includes at least a first electrode, a second electrode, and a third electrode, the method comprising:
conveying electrical stimulation energy, using a configurable sources programmed to operate as current sources, between the first electrode and the second electrode to generate a current distribution in the neural tissue
including regulating a first current flowing through the first electrode; and
regulating a first voltage at the third electrode to modify a shape of the current distribution.

13. The method of claim 12, further comprising regulating a second current through the second electrode, wherein the first electrode is an anode and the second electrode is a cathode.

14. The method of claim 13, wherein the array of electrodes includes a fourth electrode, the method further comprising regulating a third current flowing through the fourth electrode, wherein the fourth electrode is an anode, and wherein the cathode is physically located between the anodes.

15. The method of claim 13, wherein the array of electrodes includes a fourth electrode, the method further comprising regulating a second voltage at the fourth electrode, wherein the first and second electrodes are physically located between the third and fourth electrodes.

16. The method of claim 15, wherein the first and second voltages are the same.

17. The method of claim 13, wherein the first voltage is between compliance voltages on the respective first and second electrodes.

18. The method of claim 12, wherein a programmable current source is coupled to the first electrode, the method further comprising programming the current source to set the first current to a first value.

19. The method of claim 18, wherein a programmable voltage course is coupled to the third electrode, the method further comprising programming the voltage source to set the first voltage to a first value.

20. The method of claim 12, wherein the neural tissue is spinal cord tissue.

* * * * *